United States Patent
Lennon et al.

(10) Patent No.: US 6,855,311 B2
(45) Date of Patent: Feb. 15, 2005

(54) PHOTOPROTECTIVE COSMETIC COMPOSITIONS COMPRISING INORGANIC UV-BLOCKING AGENTS

(75) Inventors: Paula Lennon, Lyons (FR); Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/618,701

(22) Filed: Jul. 15, 2003

(65) Prior Publication Data

US 2004/0067208 A1 Apr. 8, 2004

Related U.S. Application Data

(63) Continuation of application No. PCT/FR02/00046, filed on Jan. 8, 2002.

(30) Foreign Application Priority Data

Jan. 15, 2001 (FR) .............................. 01 00484

(51) Int. Cl.$^7$ ............................. A61K 7/42; A61K 7/44; A61K 7/00
(52) U.S. Cl. ........................... 424/59; 424/60; 424/400; 424/401
(58) Field of Search ............................ 424/59, 60, 400, 424/401

(56) References Cited

U.S. PATENT DOCUMENTS

| | | | | |
|---|---|---|---|---|
| 5,129,972 A | * | 7/1992 | Riga et al. | 149/2 |
| 5,518,517 A | * | 5/1996 | Jahnke et al. | 71/64.08 |
| 5,858,055 A | * | 1/1999 | Jahnke et al. | 71/27 |
| 6,344,505 B1 | * | 2/2002 | Valentine et al. | 524/91 |
| 6,372,200 B2 | * | 4/2002 | Josso et al. | 424/59 |

* cited by examiner

Primary Examiner—Shelley A. Dodson
(74) Attorney, Agent, or Firm—Burns, Doane, Swecker & Mathis, L.L.P.

(57) ABSTRACT

Stable photoprotective cosmetic emulsions, notably water-in-oil emulsions well suited for the UV-photoprotection of the skin, lips, mucous membranes and/or hair, contain at least one aqueous phase, at least one oily phase, an effective UV-photoprotecting amount of at least one coated or uncoated metal oxide UV-blocking agent and an effective stabilizing amount of at least one amphiphilic oligomer or polymer derived from a polyolefin which also comprises at least one polar moiety, formulated into a physiologically acceptable medium therefor.

27 Claims, No Drawings

PHOTOPROTECTIVE COSMETIC COMPOSITIONS COMPRISING INORGANIC UV-BLOCKING AGENTS

CROSS-REFERENCE TO PRIORITY/PCT APPLICATIONS

This application claims priority under 35 U.S.C. § 119 of FR-01/00484, filed Jan. 15, 2001, and is a continuation of PCT/FR02/00046, filed Jan. 8, 2002 and designating the United States (published in the French language on Jul. 18, 2002 as WO 02/055046 A1; the title and abstract were also published in English), both hereby expressly incorporated by reference.

BACKGROUND OF THE INVENTION

1. Technical Field of the Invention

The present invention relates to a composition in the form of an emulsion comprising a mineral (inorganic) oxide and an oligomer or a polymer derived from a polyolefin, especially in the form of a water-in-oil emulsion, and to the use of said composition, especially in the cosmetics field, in particular for antisun care and/or protection of the skin, the lips and the hair.

2. Description of Background/Related/Prior Art

It is common practice in the cosmetics field to use chemical screening agents to obtain antisun products. These chemical screening agents may be introduced fairly readily into emulsions by dispersion in the oily or aqueous phase of the emulsion, depending on their lipophilic or hydrophilic nature.

To obtain high protection factors, it is necessary to increase the content of chemical screening agents. However, for reasons of tolerance, it is sought to avoid using an excessively high level of chemical screening agents, and it is preferred to introduce, alongside or in place of the chemical screening agents, mineral physical blocking agents, in particular metal oxides such as, for example, titanium dioxide and zinc oxide, which offer excellent anti-UV properties and very good skin tolerability.

However, introducing these metal oxides poses problems of cosmetic acceptability. Specifically, the antisun products containing them are often in the form of relatively thick emulsions, which are difficult to apply and to spread, heavy and sticky. In addition, with certain mineral blocking agents, for instance titanium dioxide, these defects are accompanied by a whitening effect during spreading on the skin.

Moreover, it is sought to obtain antisun emulsions that have a fluid texture, since the fluid texture makes them more practicable, easier to apply and more pleasant to use. However, fluid emulsions are also more difficult to produce with mineral blocking agents, since metal oxides have the drawback of destabilizing the emulsions into which it is desired to introduce them, and especially when they are very fluid emulsions. This difficulty of introducing metal oxides is even greater when the oxide content exceeds 1% of the final composition.

The instability phenomena are reflected in particular by the aggregation of the solid particles, the creaming and sedimentation of the emulsions, a heterogeneous appearance of the emulsions, and a change in the texture over time, this change being reflected by a thickening of the texture, which also becomes granular and heterogeneous.

SUMMARY OF THE INVENTION

The present invention seeks to overcome the above drawbacks and proposes compositions for obtaining stable emulsions, even when they are very fluid, having high protection factors by virtue of the presence of mineral (inorganic) blocking agents, and also having appreciable cosmetic acceptability.

Thus, it has now surprisingly and unexpectedly been determined that formulating into certain sunscreen compositions an oligomer or polymer derived from a polyolefin comprising at least one polar part or moiety makes it possible to achieve the desired result and especially to obtain an emulsion containing metal oxides, which have good cosmetic properties (light, fresh and also rich feel) and good stability over time, even though the emulsion is very fluid and even though it contains a large proportion of metal oxides.

Too, the present invention features compositions in the form of an emulsion, containing, in a physiologically acceptable medium, at least one aqueous phase, at least one oily phase, at least one metal oxide and at least one oligomer or one polymer derived from a polyolefin, comprising at least one polar part or moiety.

This invention also features the use of at least one oligomer or polymer derived from a polyolefin, containing at least one polar part, to stabilize an emulsion containing at least one metal oxide.

DETAILED DESCRIPTION OF BEST MODE AND SPECIFIC/PREFERRED EMBODIMENTS OF THE INVENTION

In the present application, the expression "physiologically acceptable medium" means a medium compatible with the skin, including the scalp, the mucous membranes, the eyes and/or the hair.

In the present application, the expression "composition in the form of an emulsion" means oil-in-water (O/W) emulsions containing an oily phase dispersed in an aqueous phase and water-in-oil (W/O) emulsions containing an aqueous phase dispersed in an oily phase and multiple emulsions, and for example triple (W/O/W or O/W/O) emulsions. According to a preferred embodiment of the invention, the composition is a W/O emulsion.

The compositions obtained according to the invention have the advantage of spreading easily and being absorbed quickly and completely into the skin. In addition, when they contain titanium dioxide, they have the advantage of not giving a whitening effect during application to the skin.

Moreover, the compositions according to the invention may contain a large percentage of physical blocking agents and thus give a high SPF (sun protection factor) while at the same time being entirely stable and pleasant to use.

The oligomers and polymers which can be used in the invention are known in other fields. Thus, they are described, for example, in U.S. Pat. Nos. 5,129,972 and 4,919,179, as stabilizers for explosive emulsions.

Moreover, these compounds are known as stabilizers for fertilizer compositions (see U.S. Pat. Nos. 5,518,517 and 5,858,055) in order to obtain controlled release of the fertilizer substances.

However, no document describes compositions for topical application containing such oligomers or polymers and metal oxides.

The use of oligomers or polymers derived from polyolefins as emulsifiers in the composition of the invention containing metal oxides makes it possible to obtain stable emulsions even though they are very fluid and therefore have a low viscosity.

The oligomers and polymers used in the compositions of the invention consist of a polyolefinic apolar segment and of at least one polar segment. They can have a block or comb type structure.

The polyolefinic apolar part comprises at least 40 carbon atoms and preferably from 60 to 700 carbon atoms. This apolar part may be selected from polyolefins such as oligomers, polymers and/or copolymers of ethylene, ethylene, propylene, 1-butene, isobutene, 1-pentene, 2-methyl-1-butene, 3-methyl-1-butene, 1-hexene, 1-heptene, 1-octene, 1-decene, 1-undecene, 1-dodecene, 1-tridecene, 1-tetradecene, 1-pentadecene, 1-hexadecene, 1-heptadecene and 1-octadecene. These polyolefins are hydrogenated or not.

Moreover, the oligomers or polymers derived from a polyolefin which are used in the composition of the invention comprise at least one polar part. This polar part confers amphiphilic properties on the polyolefin derivatives. Thus, these oligomers or polymers reduce the (water/oil) interfacial tension by at least 10 mN/m when they are present at a concentration of 0.01% by weight relative to the total weight of the oily phase. For example, the polyolefin with a succinic ending marketed under the name Lubrizol 2724 by Lubrizol, at a concentration of 0.01% by weight relative to the total weight of the oily phase, reduces the interfacial tension by 15 mN/m at the interface of an aqueous phase consisting of a 1% aqueous solution of $MgSO_4$, and of an oily phase comprising a mixture of oils (isohexadecane/hydrogenated polyisobutene/volatile silicone in a ratio of 8/6/4).

The polar part of the oligomers or polymers of the invention may be anionic, cationic, nonionic, zwitterionic or amphoteric. It for example comprises polyalkylene glycols or of polyalkyleneimines, or of carboxylic or dicarboxylic acids, of anhydrides thereof or of derivatives thereof, and mixtures thereof. Oligomers or polymers with a polar carboxylic acid part may be for example derived from the reaction between a polyolefin and at least one carboxylic acid or anhydride selected from the group comprising maleic acid, maleic anhydride, fumaric acid, itaconic acid, citraconic acid, mesaconic acid, aconitic acid. Preferably, the polar part consists of succinic acid or anhydride, ester or amide derivatives thereof, the corresponding salts of alkali metal, alkaline earth metal or organic salts, or alternatively of polyoxyethylene.

The oligomers or polymers derived from polyoxyethylene may be for example selected from polyisoprene-polyoxyethylene diblock polymers, poly(ethylene-co-propylene)-polyoxyethylene polymers and mixtures thereof. These polymers are described in the publication by Allgaier, Poppe, Willner, Richter (Macromolecules, 1997, Vol. 30, pp. 1582–1586).

The oligomers or polymers derived from succinic acid or anhydride may be selected in particular from the polyolefin derivatives of succinic acid or anhydride described in U.S. Pat. Nos. 4,234,435, 4,708,753, 5,129,972, 4,931,110, GB-A-2,156,799 and 4,919,179 incorporated herein for reference. The polyolefin part may consist for example of polyisobutylene, hydrogenated or not, having a molecular weight ranging from 400 to 5000. In the polyisobutylene with a succinic endgroup thus obtained, the succinic part may be esterified, amidated or in the form of a salt, that is to say that it may be modified by alcohols, amines, alkanolamines or polyols, or may be present in the form of salts of an alkali metal, alkaline-earth metal or ammonium or of an organic base such as the salts of diethanolamine and triethanolamine. The polyolefins with an esterified or amidated succinic endgroup are products of the reaction of (a) a polyolefin with a succinic ending, and of (b) an amine or an alcohol, to form an amide or an ester. The term "amine" used here comprises all types of amines including alkanol amines. This may include for example primary, secondary or tertiary monoamines, it being possible for these amines to be aliphatic, cycloaliphatic, aromatic, heterocyclic, saturated or unsaturated. Moreover, the alcohols may be mono- or polyalcohols. The monoalcohols comprise the primary, secondary or tertiary aliphatic alcohols, and phenols. The polyalcohols may be for example selected from aliphatic, cycloaliphatic, aromatic and heterocyclic polyalcohols. Polyolefins with a modified (esterified or amidated) succinic ending and their method of preparation are described in particular in U.S. Pat. No. 4,708,753 which is incorporated herein for reference.

As polyolefins with a succinic endgroup, there may be mentioned in particular polyisobutylenes with an esterified succinic ending and their salts, in particular diethanolamine salts, such as the products marketed under the names Lubrizol 2724, Lubrizol 2722 and Lubrizol 5603 by Lubrizol.

Another example of a polymeric surfactant which can be used in the invention is the product of the reaction of maleic anhydride with polyisobutylene, such as the product marketed under the name Glissopal SA by BASF.

The amount of oligomer(s) or of polymer(s) in the composition of the invention may range, for example, from 0.1% to 20% by weight of active material, preferably from 0.2% to 10% by weight and better still from 0.5% to 5% by weight relative to the total weight of the composition. It is possible to use one or more oligomers or polymers derived from polyolefins.

The metal oxides that may be used in the context of the present invention are any of those already known per se for their photoprotective activity. Thus, they may be selected especially from titanium oxide (titanium dioxide in amorphous form or crystallized in rutile and/or anatase form), zinc oxide, iron oxide, zirconium oxide or cerium oxide, or mixtures thereof.

These metal oxides may be in the form of micrometer-sized particles or nanometer-sized particles (nanopigments). In the form of nanopigments, the mean particle sizes range, for example, from 5 nm to 100 nm. Nanopigments are preferably used in the composition of the invention.

Moreover, the metal oxides may be coated or uncoated. In particular, the metal oxides may contain a hydrophobic coating. The expression "hydrophobic coating" means herein a coating having no affinity for water and which is not made wet by water. This coating is obtained by one or more surface treatments of the metal oxide with one or more hydrophobic compounds.

The coated metal oxides, in particular with hydrophobic coating, used according to the invention may have undergone, for example, one or more treatments with one or more compounds selected from alumina, silica, aluminum derivatives (for example stearate and laurate), silicon compounds (for example silicones, polydimethylsiloxanes, alkoxysilanes or siloxysilicates), sodium compounds, iron oxides, iron esters (for example stearate), fatty acids, fatty alcohols and derivatives thereof (such as stearic acid, hydroxystearic acid, stearyl alcohol, hydroxystearyl alcohol and lauryl alcohol, and derivatives thereof), lecithin, waxes (for example carnauba wax), (meth)acrylic polymers (for example polymethyl methacrylates) and fluoro compounds (for example perfluoroalkyl compounds and perfluoroalkyl ethers). The oxides may also be treated with a mixture of these compounds or they may comprise several of these successive coatings.

The metal oxides used in the composition of the invention are preferably selected from preferably coated titanium oxides and preferably coated zinc oxides, and mixtures thereof.

The uncoated titanium oxides may be for instance those sold by Tayca under the trademarks Microtitanium Dioxide MT 500 B or Microtitanium Dioxide MT 600 B; those sold by Tioxide under the trademark Selected Tioxide A-HRC or those sold by Rhodia Chimie under the trademark Mirasun TW60 (40% dispersion in water).

In particular, the metal oxides with a hydrophobic coating which may be used in the composition of the invention may be selected from titanium oxides and nanotitanium oxides treated with:

alumina and stearic acid, for instance the product sold under the name UV-Titan M160 by Kemira, and the product sold under the name ST-430C by Inanata;

polydimethylsiloxanes (PDMS), for instance the products sold under the name Eusolex T-2000 by Merck, under the name UV Titan X170 by Eckart, or under the name Si-UFTR-Z by Myoshi;

alkoxysilanes, for instance the product sold under the name Covascreen T1 by Wacker;

perfluoroalkyl compounds, for instance the product sold under the name PF-7 $TiO_2$ MT-600B by Daito;

perfluoroalkyl ethers, for instance the product sold under the name TiO2 VF-25-3A by Toshiki;

siloxysilicates, for instance the product sold under the name TSS-1 by ISK;

polymethyl methacrylates, for instance the product sold under the name PW Covasil S by Wacker;

lecithin, for instance the product sold under the name Duoterc CW 5–25 by Sachtleben;

carnauba wax, for instance the product sold under the name UVT-PT 951101 by Kemira;

silica and alumina, for instance the products sold under the names Microtitanium Dioxide MT 500 SA and Microtitanium Dioxide MT 100 SA by Tayca, and Tioveil Fin, Tioveil OP, Tioveil MOTG and Tioveil IPM by Uniqema;

alumina and aluminum stearate, for instance the product sold under the name Microtitanium Dioxide MT 100 T by Tayca;

alumina and aluminum laurate, for instance the product sold under the name Microtitanium Dioxide MT 100 S by Tayca;

iron oxides and iron stearate, for instance the product sold under the name Microtitanium Dioxide MT 100 F by Tayca;

silica, alumina and silicone, for instance the products sold under the names Microtitanium Dioxide MT 100 SAS, Microtitanium Dioxide MT 600 SAS and Microtitanium Dioxide MT 500 SAS by Tayca;

octyltrimethoxysilane, for instance the product sold under the name T-805 by Degussa;

alumina and glycerol, for instance the product sold under the name UVT-M212 by Kemira;

alumina and silicone, for instance the product sold under the name UVT-M262 by Kemira.

These hydrophobic coated titanium oxides and nanotitanium oxides may be in the form of a solid filler or in the form of a dispersion in an oily medium. Examples of dispersions of coated titanium oxide that may be mentioned include the products indicated above, sold by Uniqema under the names Tioveil FIN (nanotitanium oxide dispersed in $C_{12}$–$C_{15}$ alkyl benzoate, with a hydroxystearic acid polycondensate as dispersant) and Tioveil MOTG (nano-titanium oxide dispersed in mineral oil/triglycerides, with a hydroxystearic acid polycondensate as dispersant); the product sold under the name Covascreen T1 by Wacker (oily dispersion of TiO2 coated with trimethoxyoctylsilane at 60%); the product sold under the name Daitopersion TI-30 by Daito (dispersion of nanotitanium oxide coated with polymethylhydrogenosiloxane in cyclomethicone and dimethicone copolyol); the product sold under the name Tiosperse Ultra by Collaborative Laboratories (nanotitanium oxide coated with stearic acid/alumina, dispersed in 2-ethylhexyl hydroxystearate benzoate); the product sold under the name Mibrid Dispersion SAS4 5050 by Myoshi (nano-titanium oxide coated with alumina/stearic acid and then with polydimethylsiloxane, dispersed in cyclo-pentasiloxane); the product sold under the name SPD-T1 by Shin-Etsu (nanotitanium oxide coated with a silicone-grafted acrylic polymer and dispersed in cyclopentadimethylsiloxane).

According to one preferred embodiment of the invention, the following titanium oxides are used in the composition of the invention: SI-UFTR-Z, Tioveil MOTG, UV-Titan M160, Eusolex T-2000, PF-7 TI02 MT-600B, PW Covasil S, TSS-1, Covascreen TI, Daitopersion TI-30, Tiosperse Ultra, UV-Titan X 170, Mibrid Dispersion SAS4 5050, SPD-T1, Tioveil FIN, and more preferably the products UV-Titan X 170, Tiosperse Ultra, PW Covasil S, Mibrid Dispersion SAS4 5050 and SPD-T1.

As zinc oxides which may be used in the composition of the invention, mention may be made of for instance:

uncoated nanozinc oxides such as those sold under the name Z-cote by Sunsmart; those sold under the name Nanox by Elementis; those sold under the name Nanogard WCD 2025 by Nanophase Technologies;

coated nanozinc oxides such as for instance those sold under the name Oxide zinc CS-5 by Toshibi (ZnO coated with polymethylhydrogenosiloxane); those sold under the name Nanogard Zinc Oxide FN by Nanophase Technologies (as a 40% dispersion in Finsolv TN, $C_{12}$–$C_{15}$ alcohol benzoate); those sold under the name Daitopersion Zn-30 and Zn-50 by Daito (dispersions in cyclopolymethylsiloxane/oxyethylenated polydimethylsiloxane containing 30% or 50% of nanozinc oxides coated with silica and polymethylhydrogenosiloxane); those sold under the name NFD Ultrafine ZnO by Daikin (ZnO coated with perfluoroalkyl phosphate and perfluoroalkylethyl-based copolymer as a dispersion in cyclopentasiloxane); those sold under the name SPD-Z1 by Shin-Etsu (ZnO coated with silicone grafted acrylic polymer, dispersed in cyclodimethylsiloxane); those sold under the name Escalol Z100 by ISP (ZnO treated with alumina and dispersed in the ethylhexyl methoxycinnamate/PVP-hexadecene copolymer/methicone mixture); those sold under the name Fuji ZnO-SMS-10 by Fuji Pigment (ZnO coated with silica and polymethylsilsesquioxane); those sold under the name Nanox Gel TN by Elementis (ZnO dispersed at 55% in $C_{12}$–$C_{15}$ alcohol benzoate with hydroxy stearic acid polycondensate).

Use may also be made of a mixture of these various coated or uncoated metal oxides in the composition of the invention.

The amount of metal oxides in the composition of the invention may range, for example, from 0.5% to 30% by weight of active material, preferably from 2% to 20% by weight of active material and better still from 7% to 15% by weight of active material relative to the total weight of the composition.

The composition of the invention is intended for topical application and more particularly for application to the skin, the hair and/or the mucous membranes. It may especially constitute a cosmetic and/or dermatological composition.

The viscosity of the composition according to the invention may vary widely according to the type of product desired and may range from a very fluid milk to a compact cream. Generally, this viscosity, measured at room temperature (about 25° C.) with a Mettler RM 180 viscometer (Rheomat), ranges from 60 to 3,000 cP (centipoise) (60 to 3,000 mPa.s) and preferably from 80 to 2,500 cP (80 to 2,500 mPa.s).

According to a preferred embodiment of the invention, the composition is in the form of a W/O emulsion, especially in the form of a fluid emulsion, i.e., an emulsion having a viscosity ranging from 60 to 600 cP (60 to 600 mPa.s) and better still from 80 to 250 cP (80 to 250 mPa.s), the viscosity being measured using a Mettler RM 180 viscometer (Rheomat) with an M2 spindle, at 25° C. and at a speed of 200 rpm. For example, the value of the viscosity measured with the Mettler RM 180 viscometer (Rheomat) with an M2 spindle at 25° C. and at a speed of 200 rpm may thus range from 20 to 40 deviation units, which corresponds to a viscosity ranging from 100 to 250 cps (100 to 250 mPa.s). A fairly fluid emulsion is thus obtained, which is very pleasant to use since it spreads easily and uniformly without leaving a greasy sensation or a coarse or sticky film.

The composition according to the invention comprises an oily phase, which may be any fatty substance and especially any oil conventionally used in cosmetics. According to one preferred embodiment of the invention, the composition comprises at least one oil.

Among the oils that may be used in the composition of the invention, examples that may be mentioned include plant oils such as apricot kernel oil and soybean oil; mineral oils, for instance liquid petroleum jelly; synthetic oils, for instance isohexa-decane and cyclohexadecane; volatile or non-volatile silicone oils and fluoro oils. Volatile silicone oils that may especially be mentioned include cyclic polydimethylsiloxanes or cyclomethicones which contain from about 3 to 9 silicon atoms and preferably from 4 to 6 silicon atoms, such as cyclohexadimethylsiloxane (or cyclohexamethicone) and cyclopentadimethylsiloxane (or cyclopentamethicone), and volatile linear polydimethylsiloxanes containing from about 3 to 9 silicon atoms. According to one particular embodiment of the invention, the composition comprises at least one silicone oil.

The other fatty substances that may be present in the oily phase may be, for example, fatty acids, fatty alcohols and waxes such as petroleum jelly or beeswax.

The amount of oily phase in the composition of the invention may range, for example, from 5% to 80% and preferably from 40% to 70% by weight relative to the total weight of the emulsion. The aqueous phase of the emulsion may represent, for example, from 50% to 95% and preferably from 60% to 90% by weight relative to the total weight of the emulsion.

In a known manner, the composition of the invention may also contain adjuvants that are common in cosmetics, such as active agents, preservatives, antioxidants, complexing agents, solvents, fragrances, fillers, sunscreens, bactericides, electrolytes (such as magnesium sulfate), odor absorbers, dyestuffs and lipid vesicles. The amounts of these various adjuvants are those that are conventionally used in the field under consideration, for example from 0.01% to 20% of the total weight of the composition. Depending on their nature, these adjuvants may be introduced into the oily phase, into the aqueous phase and/or into the lipid vesicles. These adjuvants and the concentrations thereof must be such that they do not modify the desired property for the composition of the invention.

According to one preferred embodiment of the invention, the composition comprises at least one sunscreen. As sunscreens, the composition of the invention may comprise any UVA and UVB screening agents that may be used in cosmetics.

Examples of UVB-screening agents that may be mentioned include:

(1) salicylic acid derivatives, in particular homo-menthyl salicylate and octyl salicylate;

(2) cinnamic acid derivatives, in particular 2-ethyl-hexyl p-methoxycinnamate, sold by Givaudan under the name Parsol MCX;

(3) liquid β,β'-diphenylacrylate derivatives, in particular 2-ethylhexyl α-cyano-αβ'-diphenylacrylate or octocrylene, sold by BASF under the name Uvinul N539;

(4) p-aminobenzoic acid derivatives;

(5) 4-methylbenzylidene camphor sold by Merck under the name Eusolex 6300;

(6) 2-phenylbenzimidazole-5-sulfonic acid sold under the name Eusolex 232 by Merck;

(7) 1,3,5-triazine derivatives, in particular:

2,4,6-tris[p-(2'-ethylhexyl-1'-oxycarbonyl)anilino]-1,3,5-triazine sold by BASF under the name Uvinul T150, and dioctylbutamidotriazone sold by Sigma 3V under the name Uvasorb HEB;

(8) mixtures of these screening agents.

Examples of UVA-screening agents that may be mentioned include:

(1) dibenzoylmethane derivatives, in particular 4-(tert-butyl)-4'-methoxydibenzoylmethane sold by Givaudan under the name Parsol 1789;

(2) UVA-active screening agents of formula (IV) below:

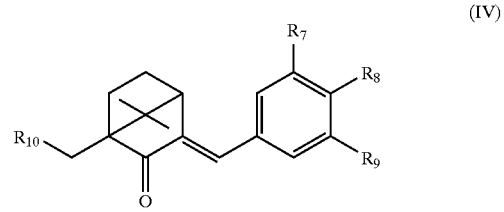

(IV)

in which:

$R_7$ and $R_9$, which may be identical or different, are each a hydrogen, a halogen, an OH radical, a saturated or unsaturated, linear or branched $C_1$–$C_{10}$ alkyl radical; a saturated or unsaturated, linear or branched $C_1$–$C_{10}$ alkoxy radical or an $HSO_3$ group;

$R_{10}$ is a hydrogen or $HSO_3$;

$R_8$ is an OH group; a group $OR_{11}$ in which $R_{11}$ is a saturated or unsaturated, linear or branched $C_1$–$C_{10}$ alkyl radical; or a group having the following structure:

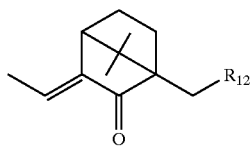

in which $R_{12}$ is hydrogen or $HSO_3$; or a group having the following structure:

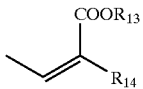

or alternatively a group having the following structure:

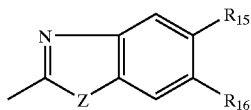

which:

Z is an oxygen atom or an —NH— radical;

$R_{13}$, $R_{14}$, $R_{15}$ and $R_{16}$, which may be identical or different, are each a hydrogen, a halogen, an OH radical, a saturated or unsaturated, linear or branched $C_1$–$C_{10}$ alkyl radical; a saturated or unsaturated, linear or branched $C_1$–$C_{10}$ alkoxy radical or an $HSO_3$ group.

A compound of formula (IV) that may be mentioned in particular is benzene-1,4-bis(3-methylidenecamphor-10-sulfonic acid) optionally in partially or totally neutralized form, which corresponds to formula (V) below:

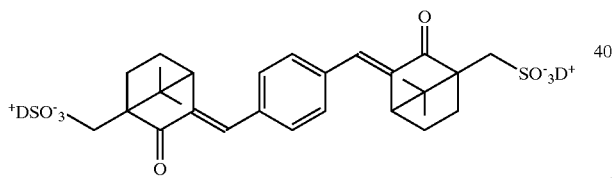

(V)

in which D is a hydrogen atom, an alkali metal or a radical $NH(R_{25})_3^+$ in which the radicals $R_{25}$, which may be identical or different, are each a hydrogen atom, a $C_1$–$C_4$ alkyl or hydroxyalkyl radical or a group $M^{n+}/n$, $M^{n+}$ denoting a polyvalent metal cation in which n is equal to 2 or 3 or 4, $M^{n+}$ preferably denoting a metal cation selected from $Ca^{2+}$, $Zn^{2+}$, $Mg^{2+}$, $Ba^{2+}$, $Al^{3+}$ and $Zr^{4+}$, and in particular benzene-1,4-bis(3-methylidene-10-camphor-sulfonic acid), sold under the name Mexoryl SX by Chimex.

(3) benzophenone derivatives, for example:

2,4-dihydroxybenzophenone (benzophenone-1);

2,2',4,4'-tetrahydroxybenzophenone (benzophenone-2);

2-hydroxy-4-methoxybenzophenone (benzophenone-3), sold under the name Uvinul M40 by BASF;

2-hydroxy-4-methoxybenzophenone-5-sulfonic acid (benzophenone-4) and also its sulfonate form (benzophenone-5), sold by BASF under the name Uvinul MS40;

2,2'-dihydroxy-4,4'-dimethoxybenzophenone (benzophenone-6);

5-chloro-2-hydroxybenzophenone (benzophenone-7);

2,2'-dihydroxy-4-methoxybenzophenone (benzophenone-8);

the disodium salt of 2,2'-dihydroxy-4,4'-dimethoxybenzophenone-5,5'-disulfonic acid (benzophenone-9);

2-hydroxy-4-methoxy-4'-methylbenzophenone (benzophenone-10);

benzophenone-11;

2-hydroxy-4-(octyloxy)benzophenone (benzophenone-12).

(4) silane derivatives or polyorganosiloxanes containing a benzophenone group;

(5) anthranilates, in particular menthyl anthranilate sold by Haarman & Reimer under the name Neo Heliopan MA;

(6) compounds comprising per molecule at least two benzoazolyl groups or at least one benzodiazolyl group, in particular phenylene-1,4-bis(benzimidazolyl-3,3',5,5'-tetrasulfonic acid) and also the salts thereof, of structure (VI) below:

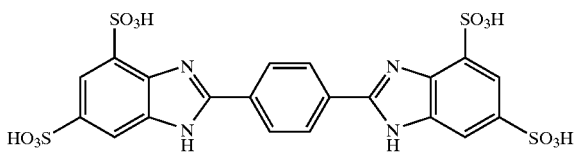

(VI)

sold by Haarman & Reimer;

(7) silicon derivatives of N-substituted benzimidazolylbenzazoles or of benzofurylbenzazoles, and in particular:

2-[1-[3-[1,3,3,3-tetramethyl-1-[(trimethylsilyl)oxy]-disiloxanyl] propyl]-1H-benzimidazol-2-yl] benzoxazole;

2-[1-[3-[1,3,3,3-tetramethyl-1-[(trimethylsilyl)oxy]-disiloxanyl] propyl]-1H-benzimidazol-2-yl] benzothiazole;

2-[1-(3-trimethylsilanylpropyl)-1H-benzimidazol-2-yl] benzoxazole;

6-methoxy-1,1'-bis(3-trimethylsilanylpropyl)-1H,1'H-[2,2']bibenzimidazolylbenzoxazole;

2-[1-(3-trimethylsilanylpropyl)-1H-benzimidazol-2-yl]-benzothiazole; which are described in EP-A-1,028,120;

(8) triazine derivatives, and in particular 2,4-bis{[4-(2-ethylhexyloxy)-2-hydroxy]phenyl}-6-(4-methoxyphenyl)-1,3,5-triazine sold by Ciba Geigy under the name Tinosorb S, and 2,2'-methylenebis[6-(2H-benzotriazol-2-yl)-4-(1,1,3,3-tetramethylbutyl) phenol] sold by Ciba Geigy under the name Tinosorb M;

(9) mixtures thereof.

A mixture of several of these screening agents and a mixture of UVB-screening agents and of UVA-screening agents may also be used.

The composition according to the invention is useful in numerous treatments, especially cosmetic treatments, of the skin, the lips and the hair, including the scalp, especially for protecting and/or caring for the skin, the lips and/or the hair and/or for making up the skin and/or the lips.

The composition according to the invention may be used, for example, as an antisun care and/or protection product for the face and/or the body in the form of creams or milks.

Thus, a subject of the invention is also the cosmetic use of the composition as defined above for the antisun care and/or protection of the skin, the lips and/or the hair, and/or for making up the skin and/or the lips.

A subject of the invention is also a cosmetic treatment process for protecting the skin, including the scalp, the hair and/or the lips against solar radiation, characterized in that it consists in applying to the skin, the hair and/or the lips a composition as defined above.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

W/O Emulsion of SPF 30

Oily Phase:

| | |
|---|---|
| Polyisobutylene with an esterified succinic ending, diethylethanolamine salt (Lubrizol 5603) | 3% |
| Cyclohexadimethylsiloxane | 20% |
| Isohexadecane | 30% |
| PDMS-coated titanium dioxide (UV Titan X170 from the company Kemira) | 10% (A.M.) |

Aqueous Phase:

| | |
|---|---|
| Preservatives | qs % |
| Mexoryl SX (water-soluble screening agent) | 3% |
| Demineralized water | qs 100% |

Procedure: Each of the two phases is homogenized and they are then mixed together with stirring, dispersing the aqueous phase in the oily phase.

A very soft fluid milk is obtained, which does not whiten on application. It has a fine, uniform appearance under a microscope and good dispersion of the pigments is observed.

This emulsion remains stable after storage for two months at 45° C. It can be used as a protective daily care and as an antisun cream for the face and the body.

EXAMPLE 2

W/O Emulsion of SPF 40

Oily Phase:

| | |
|---|---|
| Polyisobutylene with an esterified succinic ending, diethylethanolamine salt (Lubrizol 5603) | 3% |
| Cyclohexadimethylsiloxane | 30% |
| Isohexadecane | 25% |
| Ethylhexyl methoxycinnamate | 7% |
| PDMS-coated titanium dioxide (UV Titan X170 from the company Kemira) | 10% (A.M.) |

Aqueous Phase:

| | |
|---|---|
| Preserving agent | qs |
| Mexoryl SX (water-soluble screening agent) | 3% |
| Water | qs 100% |

Procedure: The two phases are homogenized and the emulsion is then prepared with stirring, dispersing the aqueous phase in the oily phase.

A very soft fluid milk is obtained, which does not whiten the skin on application. It has a fine, uniform appearance under a microscope and good dispersion of the pigments is observed.

This emulsion remains stable after storage for two months at 45° C. It can be used as a protective daily care and as an antisun cream for the face and the body.

EXAMPLE 3

W/O Emulsion of SPF 30

Oily Phase:

| | |
|---|---|
| Polyisobutylene with an esterified succinic ending, diethylethanolamine salt (Lubrizol 5603) | 3% |
| Cyclohexadimethylsiloxane | 10% |
| Isohexadecane | 25% |
| Ethylhexyl methoxycinnamate | 7% |

Aqueous Phase:

| | |
|---|---|
| Preserving agent | qs |
| Mexoryl SX (water-soluble screening agent) | 3% |
| Nanotitanium oxide at 30% in water (Mirasun TIW 60 from the company Rhodia) | 10% |
| Water | qs 100% |

Procedure: The two phases are homogenized and the emulsion is then prepared with stirring, dispersing the aqueous phase in the oily phase.

A very soft fluid milk is obtained, which has the advantage that it does not whiten on application to the skin. It has a fine, uniform appearance under a microscope and good dispersion of the pigments is observed.

This emulsion remains stable after storage for two months at 45° C. It can be used as a protective daily care and as an antisun cream for the face and the body.

EXAMPLE 4

W/O Emulsion of SPF 20

Oily Phase:

| | |
|---|---|
| Polyisobutylene with an esterified succinic ending, diethylethanolamine salt (Lubrizol 5603) | 3% |
| Cyclohexadecane | 5% |
| Mineral oil | 10% |
| 2-Ethylhexyl methoxycinnamate | 7% |
| Benzophenone-3 | 2% |
| Zinc oxide coated with a silicone graft acrylic polymer, dispersed in cyclodimethylsiloxane (SPD Z1 from Shin-Etsu) | 25% |

Aqueous Phase:

| | |
|---|---|
| Preserving agent | qs |
| Magnesium sulfate | 1% |
| Water | qs 100% |

Procedure: The two phases are homogenized and the emulsion is then prepared with stirring, dispersing the aqueous phase in the oily phase.

A very soft fluid milk/cream is obtained, which has the advantage that it does not whiten on application to the skin.

It has a fine, uniform appearance under a microscope and good dispersion of the pigments is observed.

This emulsion remains stable after storage for two months at 45° C. It can be used as a day cream.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective cosmetic emulsion comprising at least one aqueous phase, at least one oily phase, an effective UV-photoprotecting amount of at least one metal oxide UV-blocking agent and an effective stabilizing amount of at least one amphiphilic oligomer or polymer derived from a polyolefin which also comprises at least one polar moiety, formulated into a physiologically acceptable medium therefor.

2. The photoprotective cosmetic emulsion as defined by claim 1, said at least one amphiphilic oligomer or polymer derived from a polyolefin comprising a polyolefinic apolar moiety having at least 40 carbon atoms.

3. The photoprotective cosmetic emulsion as defined by claim 1, said at least one amphiphilic oligomer or polymer derived from a polyolefin comprising a polyolefinic apolar moiety having from 60 to 700 carbon atoms.

4. The photoprotective cosmetic emulsion as defined by claim 2, said polyolefinic apolar moiety comprising an oligomer, polymer and/or copolymer of ethylene, propylene, 1-butene, isobutene, 1-pentene, 2-methyl-1-butene, 3-methyl-1-butene, 1-hexene, 1-heptene, 1-octene, 1-decene, 1-undecene, 1-dodecene, 1-tridecene, 1-tetradecene, 1-pentadecene, 1-hexadecene, 1-heptadecene or 1-octadecene.

5. The photoprotective cosmetic emulsion as defined by claim 1, said at least one oligomer or polymer derived from a polyolefin reducing the interfacial tension thereof by at least 10 mN/m when said oligomer or polymer is present at a concentration of 0.01% by weight relative to the weight of the oily phase.

6. The photoprotective cosmetic emulsion as defined by claim 1, said at least one polar moiety being anionic, cationic, nonionic, zwitterionic or amphoteric.

7. The photoprotective cosmetic emulsion as defined by claim 1, said at least one polar moiety comprising a polyalkylene glycol, polyalkyleneimine, carboxylic or dicarboxylic acid, anhydride or derivative thereof, or mixture thereof.

8. The photoprotective cosmetic emulsion as defined by claim 1, said at least one polar moiety comprising polyoxyethylene, succinic acid or anhydride or derivative thereof.

9. The photoprotective cosmetic emulsion as defined by claim 1, said at least one oligomer or polymer derived from a polyolefin comprising the reaction product between a polyolefin derivative and at least one acid selected from the group consisting of maleic acid; maleic anhydride; fumaric acid; itaconic acid; citraconic acid; mesaconic acid; aconitic acid; derivatives and mixtures thereof.

10. The photoprotective cosmetic emulsion as defined by claim 1, said at least one oligomer or polymer derived from a polyolefin comprising a polyisobutylene with an optionally modified succinic endgroup.

11. The photoprotective cosmetic emulsion as defined by claim 1, said at least one oligomer or polymer derived from a polyolefin comprising the product of the reaction of maleic anhydride with polyisobutylene.

12. The photoprotective cosmetic emulsion as defined by claim 1, the amount of said at least one oligomer or polymer derived from a polyolefin ranging from 0.1% to 20% by weight of active material relative to the total weight of the composition.

13. The photoprotective cosmetic emulsion as defined by claim 1, said at least one metal oxide comprising a titanium, zinc, iron, zirconium or cerium oxide or mixture thereof.

14. The photoprotective cosmetic emulsion as defined by claim 13, said at least one metal oxide comprising a nanopigment thereof.

15. The photoprotective cosmetic emulsion as defined by claim 1, said at least one metal oxide having been coated with one or more compounds of alumina, silica, aluminum, silicon, sodium, iron, fatty acid, fatty alcohol or derivative thereof, lecithin, wax, (meth)acrylic polymer and/or fluoro compound.

16. The photoprotective cosmetic emulsion as defined by claim 1, the amount of said at least one metal oxide ranging from 0.5% to 30% by weight of active material relative to the total weight of the composition.

17. The photoprotective cosmetic emulsion as defined by claim 1, further comprising at least one other UV-sunscreen.

18. The photoprotective cosmetic emulsion as defined by claim 1, said at least one oily phase comprising from 5% to 80% by weight relative to the total weight of the composition.

19. The photoprotective cosmetic emulsion as defined by claim 1, comprising a water-in-oil emulsion.

20. The photoprotective cosmetic emulsion as defined by claim 1, formulated as a makeup.

21. The photoprotective cosmetic emulsion as defined by claim 1, formulated as a cream or milk.

22. The photoprotective cosmetic emulsion as defined by claim 1, having a viscosity ranging from 60 to 3,000 cP.

23. The photoprotective cosmetic emulsion as defined by claim 22, having a viscosity ranging from 80 to 2,500 cP.

24. The photoprotective cosmetic emulsion as defined by claim 22, having a viscosity ranging from 60 to 600 cP.

25. The photoprotective cosmetic emulsion as defined by claim 24, having a viscosity ranging from 80 to 250 cP.

26. A regime or regimen for the UV-photoprotection of the skin, lips, mucous membranes and/or hair, comprising topically applying thereon a photoprotective cosmetic emulsion which comprises at least one aqueous phase, at least one oily phase, an effective UV-photoprotecting amount of at least one metal oxide UV-blocking agent and an effective stabilizing amount of at least one amphiphilic oligomer or polymer derived from a polyolefin which also comprises at least one polar moiety, formulated into a physiologically acceptable medium therefor.

27. A method for stabilizing a photoprotective emulsion comprising at least one UV-blocking metal oxide, which comprises formulating therein an effective stabilizing amount of at least one amphiphilic oligomer or polymer derived from a polyolefin and which also comprises at least one polar moiety.

* * * * *